(12) United States Patent
Cofer et al.

(10) Patent No.: US 10,265,498 B1
(45) Date of Patent: *Apr. 23, 2019

(54) SYSTEMS AND METHODS FOR DETECTING AND ALERTING A DROWSY DRIVER

(71) Applicant: BEIJING SHUNYUAN KAIHUA TECHNOLOGY LIMITED, Haidian District, Beijing (CN)

(72) Inventors: Ashton Cameron Cofer, Gahanna, OH (US); Julia Nicole Bray, New Albany, OH (US); Luke David Clay, Gahanna, OH (US); Grace Ann Harrison, Gahanna, OH (US)

(73) Assignee: BEIJING SHUNYUAN KAIHUA TECHNOLOGY LIMITED, Haidian District, Beijing (CN)

( * ) Notice: Subject to any disclaimer, the term of this patent is extended or adjusted under 35 U.S.C. 154(b) by 0 days.

This patent is subject to a terminal disclaimer.

(21) Appl. No.: 15/919,320

(22) Filed: Mar. 13, 2018

Related U.S. Application Data

(63) Continuation of application No. 15/141,901, filed on Apr. 29, 2016, now Pat. No. 9,937,791.

(60) Provisional application No. 62/154,189, filed on Apr. 29, 2015.

(51) Int. Cl.
*A61M 21/00* (2006.01)
*A61B 5/00* (2006.01)
*A61B 5/18* (2006.01)
*G08B 21/06* (2006.01)
*A61B 5/024* (2006.01)

(52) U.S. Cl.
CPC ............. *A61M 21/00* (2013.01); *A61B 5/002* (2013.01); *A61B 5/18* (2013.01); *G08B 21/06* (2013.01); *A61B 5/024* (2013.01); *A61M 2021/005* (2013.01); *A61M 2021/0027* (2013.01); *A61M 2021/0083* (2013.01); *A61M 2205/3584* (2013.01)

(58) Field of Classification Search
CPC ....................................................... A61M 21/00
USPC .......................................................... 340/575
See application file for complete search history.

(56) References Cited

U.S. PATENT DOCUMENTS

| | | | |
|---|---|---|---|
| 2012/0296226 A1* | 11/2012 | Su ........................... | A61B 5/024 600/508 |
| 2014/0276090 A1* | 9/2014 | Breed ...................... | A61B 5/18 600/473 |
| 2016/0195657 A1* | 7/2016 | Asakawa ............... | B82Y 20/00 359/352 |

* cited by examiner

*Primary Examiner* — Eric Blount
(74) *Attorney, Agent, or Firm* — Young Basile Hanlon & MacFarlane, P.C.

(57) ABSTRACT

Systems and methods are provided for detecting and preventing sleep onset in a user. The method can include, for example, monitoring the user's heart rate, establishing a baseline average heart rate over a period of time, establishing a threshold heart rate that is less than the baseline average heart rate, detecting a drop in the user's heart rate below the threshold, and in response to detecting the drop, initiating a sleep prevention program.

20 Claims, 3 Drawing Sheets

SYSTEMS AND METHODS FOR DETECTING AND ALERTING A DROWSY DRIVER

PRIORITY

This application is a continuation application of U.S. patent application Ser. No. 15/141,901, filed Apr. 29, 2016, which claims priority to U.S. Provisional Patent Application No. 62/154,189, filed Apr. 29, 2015, both of which are hereby incorporated by reference in their entirety.

BACKGROUND

Every year, drowsy driving kills about 1,500 people and injures about 71,000 more in the United States alone. Sixty percent of drivers, or about 168 million people, admit to driving a vehicle while drowsy in the past year. Over 100 million people have experienced falling asleep at the wheel.

Current solutions to drowsy driving have proven inadequate. Some solutions involve tracking a driver's eyes to determine whether the driver is falling asleep. More specifically, these tracking systems can determine whether a driver is looking at the road, and if he or she is not, the system can alert the driver to cause them to wake up. However, systems that track the driver's eyes fail to alert the driver soon enough. By the time the system detects that a driver is asleep, it is too late—the driver may have already lost control of the vehicle.

Similar limitations exist with respect to solutions that monitor the position and/or movement of a driver's head. Some of these systems use accelerometers attached to the driver's head, for example via an earpiece, to determine whether the driver's head has dropped as a result of sleep onset. Again, however, these systems cannot detect sleep until it is too late. Furthermore, these solutions are bulky and uncomfortable to wear, causing drivers to avoid using them in the first place.

In order to maintain a safe driving condition, a driver must remain awake, rather than being woken up immediately after falling asleep. For at least these reasons, a need exists for detecting and alerting a drowsy driver. More specifically, a need exists for detecting a pre-sleep indicator and intervening to prevent sleep onset from occurring at all.

SUMMARY

Both the foregoing general description and the following detailed description are exemplary and explanatory only. The claims are not intended to be limited to the descriptions and examples herein.

In an example, a method is provided for detecting and preventing sleep onset in a user. The term "sleep onset" is used to describe the transition from wakefulness into sleep or drowsiness, and can be used to apply to any portion of that transition. The term "drowsiness" is used to describe a state in which an individual is not yet asleep, but may not be exhibiting an alertness associated with wakefulness. The method for detecting and preventing sleep onset can be used in any scenario, such as during driving. However, the method can also apply to other scenarios such as piloting a boat or aircraft, or performing a job that involves sitting in a stationary position. The terms "user" and "driver" are intended to be used interchangeably, and both terms can apply to scenarios that do not involve driving.

The method can include monitoring the user's heart rate. This can be accomplished in a variety of manners; for example, the user can wear a heart-rate monitor. Suitable heart-rate monitors include the heart-rate measuring products from MIO GLOBAL. However, any type of heart-rate measuring product can be used; for example, wrist bands, wrist watches, chest straps, fingertip sensors, and so on.

The method can also include establishing a baseline average heart rate over a period of time. This can be accomplished by, for example, averaging the user's heart rate over a 3-minute period of time. Other time periods may be used as well, such as 4 or 5 minutes. In some examples, the baseline average heart rate can be reestablished after a set period of time, such as 3, 4, or 5 minutes.

After establishing the baseline average, the method can also include establishing a threshold heart rate that is less than the baseline average heart rate. For example, the threshold heart rate can be calculated as a percentage of the baseline average heart rate.

After establishing the threshold heart rate, the method can include detecting a drop in the user's heart rate below that threshold. This drop can provide a pre-sleep indicator, which indicates the onset of sleep. In response to detecting the drop, the method can include initiating a sleep prevention program to prevent the user from falling asleep.

A system is also disclosed for detecting and preventing sleep onset in a user. The system can include a heart rate monitor coupled to the user, a non-transitory, computer-readable medium that contains instructions, and a processor communicatively coupled to the heart rate monitor.

The processor can execute instructions to perform stages, such as monitoring the user's heart rate, establishing a baseline average heart rate over a period of time, establishing a threshold heart rate that is less than the baseline average heart rate, detecting a drop in the user's heart rate below the threshold, and in response to detecting the drop, initiating a sleep prevention program.

The sleep prevention program included in an example method or system can include a variety of different strategies for keeping a user awake. In one example, the sleep prevention program includes displaying an alert on a display, e.g. a display in a vehicle. In another example, the sleep prevention program includes playing a sound through at least one speaker, e.g. a speaker in a vehicle or headset. In yet another example, the sleep prevention program includes initiating a responsive or verbal-based game with the user. In one example, the sleep prevention program includes initiating a telephone call from the user to a contact of the user. In another example, the sleep prevention program includes conducting a virtual conversation with the user. In yet another example, the sleep prevention program includes displaying a blue light, with wavelengths between about 450 nm and 495 nm.

DESCRIPTION OF THE EXAMPLES

Reference will now be made in detail to the present examples, including examples illustrated in the accompanying drawings. Wherever possible, the same reference numbers will be used throughout the drawings to refer to the same or like parts.

Figure 1:
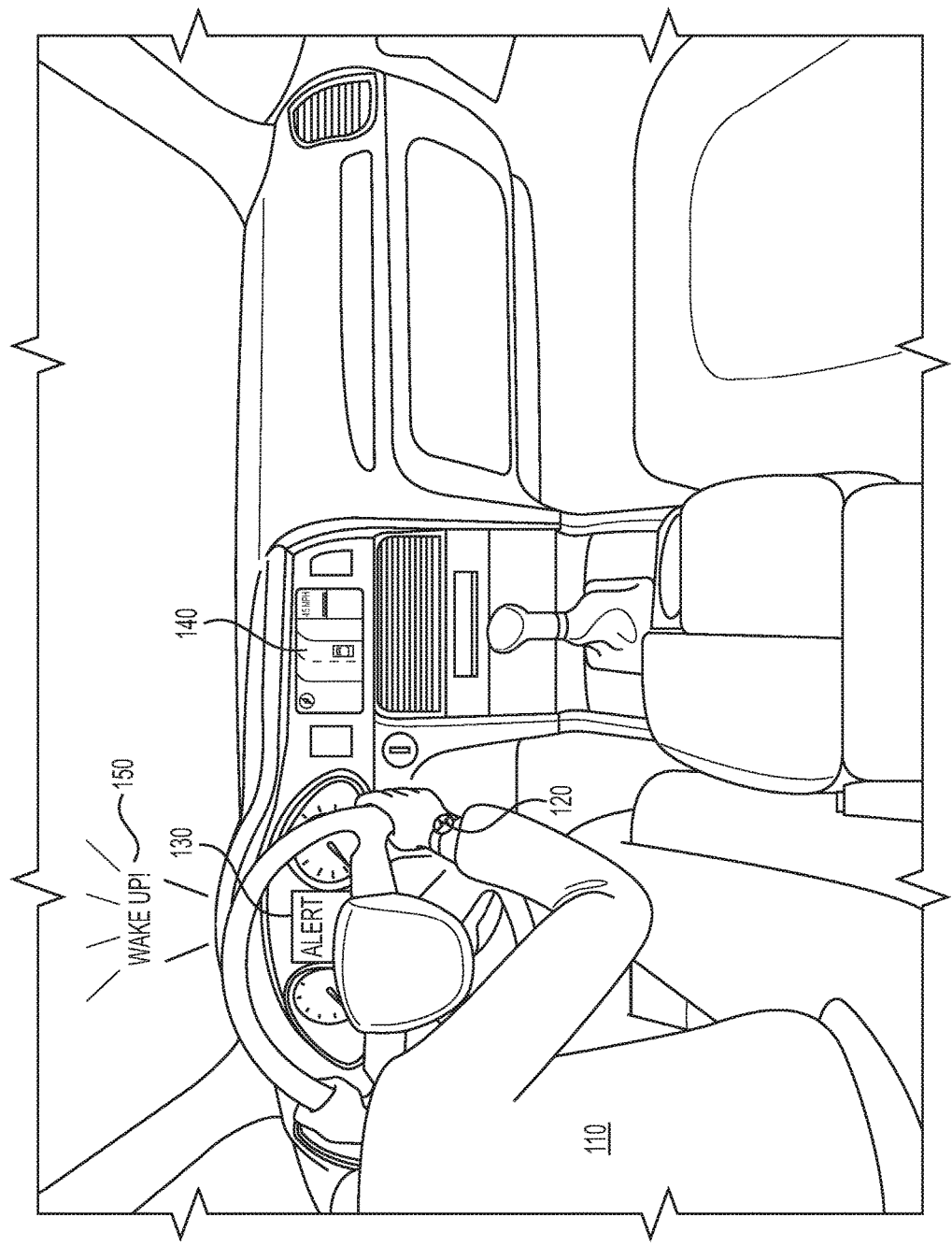
FIG. 1 is an exemplary illustration of a system for detecting and preventing sleep onset, implemented in a vehicle.

Examples described herein include systems and methods for detecting and preventing sleep onset in a user. FIG. 1 provides an example illustration of such a system implemented in a vehicle. In the example of FIG. 1, a user 110 is driving a vehicle equipped with a system for detecting and preventing sleep onset.

As shown in FIG. 1, the user 110 can wear a heart-rate monitor 120 to monitor the user's 110 heart rate. Any type of heart-rate measuring product can be used; for example, wrist bands, wrist watches, chest straps, fingertip sensors, and others. The heart-rate monitors 120 made by MIO GLOBAL are particularly suitable for this purpose because they are robust, lightweight, affordable, and provide connectivity with other applications or devices. In the example of FIG. 1, the heart-rate monitor 120 includes wireless connectivity such that the heart-rate monitor 120 can connect to a processor within the vehicle. Most modern vehicles have the ability to wirelessly connect to devices, such as smartphones, via BLUETOOTH, Wi-Fi, or other wireless protocols.

In some examples, the heart-rate monitor 120 must be enrolled with the vehicle's computing system in order to allow for wireless communication between the heart-rate monitor 120 and the vehicle. The enrollment process prevents the vehicle from connecting to a wireless device located outside the vehicle, such as devices carried in other vehicles on the road. However, once the heart-rate monitor 120 is enrolled with a particular vehicle, the vehicle can automatically recognize and connect to the heart-rate monitor 120 in the future. In some examples, the vehicle can automatically recognize and connect to a heart-rate monitor 120, and automatically run a program for detecting and preventing sleep onset in a user 110.

Once connected to a heart-rate monitor 120 being worn by a user 110, the system can establish a baseline average heart rate for the user 110. For example, a processor within the vehicle can calculate the baseline average heart rate for the user 110. In one example, the baseline average is an average of the user's 110 heart rate over a defined period of time. Any period of time may be used. Suitable time periods include, for example, time periods between 2 minutes and 10 minutes. In some examples, a mean averaging method is used to calculate the baseline average. In other examples, a median averaging method is used to calculate the baseline average.

In some embodiments, the sampling period for calculating the baseline average may be delayed some predetermined period from the time the user entered the vehicle or commenced driving. The user may have been engaged in some physical activity (e.g., walking, running, or carrying items) prior to entering the vehicle. As a result, calculating the baseline average based on data collected immediately upon the user's entering the vehicle could yield an artificially high baseline average. The predetermined period of time during which sampling is delayed may be any suitable period adequate to account for full recovery from physical exertion, such as 5, 10, or 15 minutes.

In embodiments where the user was wearing heart rate monitor 120 prior to entering the vehicle, a period of increased physical activity and a level of such activity may be detected by monitor 120. A determination that the user is engaged in increased physical activity can be made based, at least in part, on the user's detected heart rate, a step count rate, accelerometers within monitor 120, or some other suitable functionality of monitor 120. The predetermined period of time during which sampling is delayed may be based, at least in part, on the degree of physical exertion detected prior to the user entering the vehicle. For example, when high physical exertion has been detected, the sampling period may be delayed a first period of time whereas when relatively low physical exertion has been detected, the sampling period may be delayed a second period of time shorter than the first period of time.

In still further embodiments, heart rate monitor may "learn" user's resting or baseline heart rate over time, such that the sampling period and/or a calculation of the baseline heart rate is no longer needed each time the user enters the vehicle.

After establishing the baseline average, the processor within the vehicle can calculate a threshold heart rate. The threshold heart rate can indicate that a user 110 is experiencing sleep onset. As a result, the threshold heart rate can be set lower than the baseline average heart rate. For example, the threshold heart rate can be a percentage of the baseline average heart rate. Any percentage that indicates sleep onset may be used. For example, the threshold heart rate can be chosen as 90% of the baseline average heart rate. Other percentages can be used, such as between 80-95%. The particular percentage can be optimized for different users 110 based on feedback or other information from individual users 110. In other examples, the threshold heart rate can be calculated by subtracting a set number from the average heart rate. For example, the threshold heart rate can be calculated by subtracting 10 beats per minute from the baseline average heart rate.

In another embodiment, in addition to wearing heart-rate monitor 120 while driving, the user may also wear the heart-rate monitor 120 while the user is asleep at night. In such instances, monitor 120 may "learn" the user's sleeping heart rate. Thus, the threshold heart rate can be set to the user's average sleeping heart rate or can otherwise be based, at least in part, on the user's average sleeping heart rate (i.e., a heart rate within 10% or 10 beats per minute of the user's average sleeping heart rate).

Although the "threshold heart rate" is described as a value that reflects actual heart rate, it can also be a value that reflects a drop in heart rate relative to the baseline average heart rate. The drop can be described in absolute terms (e.g., 10 beats per minute slower than the baseline average rate) or in proportional terms (e.g., 10% lower than the baseline average rate).

Regardless of how the threshold heart rate is obtained, it can be used to provide a pre-sleep indicator. Applicant's research has shown that a person's heart rate decreases immediately before falling asleep. Therefore, initiating a sleep prevention program at the right time can prevent a user from falling asleep at the wheel and causing an accident. In one example, this is accomplished by initiating a sleep prevention program upon detecting a drop in the user's 110 heart rate that falls below the threshold heart rate.

A variety of sleep prevention techniques can be included in the sleep prevention program. In the example of FIG. 1, two such techniques are shown. First, a primary display 130 is shown displaying an alert to the user 110, indicating that the user 110 is becoming drowsy and/or needs to take corrective action to avoid sleep. Although the alert on the primary display 130 shows the word "ALERT," it can include any text or graphics to provide the user 110 with appropriate information to keep the user 110 awake or provide further information about utilizing the sleep prevention program. For example, the primary display 130 can read "You are getting tired. Please pull over at the next opportunity." In some examples, the primary display 130 can provide the user 110 with various options for continuing the sleep prevention program, described in more detail below.

FIG. 1 includes a heads-up display 150. The heads-up display 150 can be used in place of, or in addition to, the primary display 130. In this example, the heads-up display 150 instructs the user 110 to "WAKE UP," providing an important message directly in the user's 110 line of sight. As with the primary display 130, the heads-up display 150 can include any type of text or graphics that might help keep the user 110 awake or provide further information about utilizing the sleep prevention program.

FIG. 1 also depicts a secondary display 140, which can be used for similar purposes as the primary display 130 and heads-up display 150. The secondary display 140 can provide additional information, such as options for various tasks within the sleep prevention program. Alternatively, the secondary display 140 can provide duplicative information as either the primary display 130 or heads-up display 150. Finally, the secondary display 140 can be used as the only display related to the sleep prevention program in some examples.

In some examples, the system incorporates the use of blue light as part of the sleep prevention program. Studies have shown that blue light stimulates a human's pineal gland in the brain, which reduces the amount of melatonin released in the body, thereby reducing drowsiness. For examples, wavelengths between about 450 nm and 495 nm can reduce drowsiness in a driver.

The primary display 130, secondary display 140, and/or heads-up display 150 can be used to implement the blue-light feature mentioned above. For example, when the system detects a drop in the user's 110 heart rate that falls below the threshold heart rate, any of these displays 130, 140, 150 can emit blue light having wavelengths at least between about 450 nm and 495 nm. The light can be emitted on one, two, or all three displays. In some examples, the system includes a separate light fixture mounted in the vehicle and dedicated to emitting blue light when the user 110 becomes drowsy. In any case, the light can be emitted momentarily, in a flashing manner, or can stay on for a period of time.

The blue light feature can be incorporated into other features. For example, the "ALERT" message shown on the primary display 130 can be displayed in blue, or against a blue background. In other examples, the interface with the system (e.g., for playing a voice-based game) can include blue light. In yet other examples, a user's 110 personal device (e.g., smartphone, tablet, watch) can emit the blue light. Moreover, for any of the uses described above with respect to the various displays 130, 140, and 150 can be carried out—either alternatively or in addition—on the heart-rate monitor 120 itself. That is, the heart-rate monitor 120 can display alerts, display a blue light, and so on.

In one example, the sleep prevention program includes playing a sound. The sound can be played in addition to the use of the various displays 130, 140, and 150. However, in some examples the sound can be played as an alternative to a visual display. The sound can be made in a variety of ways. In some examples, where the user 110 has paired their heart-rate monitor 120 with a vehicle, the vehicle can play the sound via one or more speakers installed in the vehicle. In other examples, the user's 110 heart-rate monitor 120 makes the sound. In yet another example, the user's 110 personal device can make the sound. This may be useful in scenarios where the user's 110 personal device is paired with the heart-rate monitor 120. Additionally, the user's 110 personal device can cause the vehicle the play the sound via a vehicle speaker; for example, the personal device can connect to the vehicle's computer via a BLUETOOTH connection.

In another example, the sleep prevention program can include other integrated functions of the vehicle, such as turning down the temperature and/or increasing the fan speed of the vehicles air conditioning unit, vibrating the steering wheel or user's seat, turning on the interior car lamps, turning up the volume of the vehicle's stereo, or activating the windshield wipers. Of course, these are just examples and additional or alternative integrated functions of the vehicle can be incorporated into the sleep prevention program.

The sleep prevention program can also include various interactive activities. Each of the activities described below can be implemented through a computer built into the vehicle or some other type of computing device, such as a user's 110 personal device or heart-rate monitor 120. While some examples below describe a personal device, those examples apply equally to monitor 120 or a computer within a vehicle or other vehicle.

In one example, the sleep prevention program includes an interactive activity such as a responsive or verbal-based game. The vehicle's computer (or user's 110 personal device, as explained earlier) can initiate a verbal-based game, such as "twenty questions" or brain teasers, to keep the user 110 alert and prevent drowsiness. Any type of games may be used; however, games that can be initiated and/or played purely through a user's 110 voice are ideal, as the user 110 would not need to avert their eyes from the road.

In another example, the sleep prevention program includes a virtual conversation with the vehicle's computer, the user's 110 personal device, or monitor 120. In that example, the user 110 can conduct a virtual conversation with a "bot," such as SIRI, that simulates a conversation by asking questions to the user 110, responding to the user's 110 statements, and so on.

In yet another example, the sleep prevention program includes suggesting or initiating a phone call with one of the user's 110 contacts. In instances where the user's 110 personal device is paired with the heart-rate monitor 120 and/or the vehicle, the system can access the user's 110 contact list within the personal device and suggest one or more contacts to call. For example, the system can recommend calling the user's 110 favorite contact, a contact predetermined by the user, or a list of the top five most commonly called contacts. The user 110 can verbally indicate which contact he or she would like to call, and the personal device or vehicle can initiate the call.

In another example, the sleep prevention program includes suggesting or initiating a phone call with another drowsy driver. For example, the user's 110 personal device and/or vehicle can communicate with a server, indicating that the user 110 is becoming drowsy. As part of the sleep prevention program, the system can obtain contact information, from the server, of another drive that has recently entered a similar sleep prevention program while driving. For example, the user 110 can be connected to a second user that became drowsy five minutes earlier, and is currently conducting a virtual conversation as part of a sleep prevention program. The five-minute time period is merely exemplary and can be modified as necessary.

Figure 2:
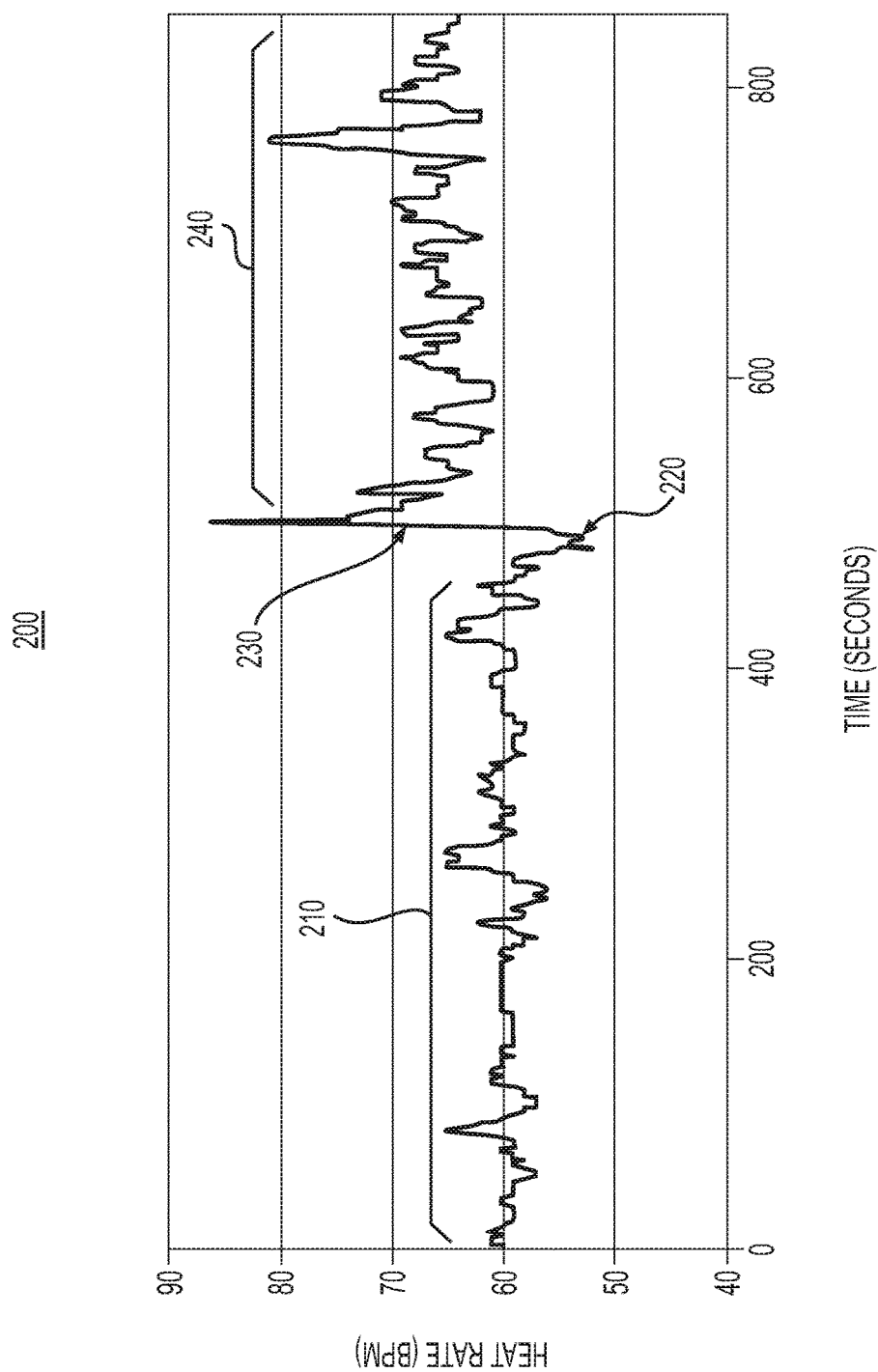
FIG. 2 is an exemplary graph of a driver's heart rate over time in a drowsy driving scenario that includes an alert for the driver.

FIG. 2 is an exemplary graph 200 of a driver's heart rate over time. The graph 200 depicts the driver's heart rate over period of time that spans normal driving, a pre-sleep indicator of sleep onset, and subsequent sleep prevention activities. The driver's heart rate is measured in beats per minute, and can be collected via a heart-rate monitor such as the one disclosed with respect to FIG. 1.

In portion 210, the driver's heart rate maintains a fairly steady state, fluctuating between about 58-64 beats per minute. During this period of the time, the system can calculate a baseline average heart rate. In this example, the baseline average heart rate may be calculated as approximately 60 beats per minute. Portion 210 spans approximately seven minutes. After the first three minutes, the baseline average heart rate can be calculated. Every minute after, a new baseline average heart rate can be calculated, reflecting the previous three minutes. As explained earlier, different periods of time may be used instead of three minutes—such as one, two, four, or five minutes, or any other amount of time. Further, the period of time elapsed between recalculating the baseline average heart rate need not be limited to one minute. Instead, the baseline average heart rate can be recalculated as often as desired—for example, every 20 seconds, 30 seconds, two minutes, or any other period of time. Shorter time periods can provide greater accuracy, but a time period that is too short may not be able to appropriately recognize a pre-sleep indicator.

In one example, each time the baseline average heart rate is calculated, a threshold heart rate is also calculated. The threshold heart rate can be calculated as a percentage of the baseline heart rate, or as a percentage change in the baseline heart rate. For example, the threshold heart rate can be calculated as 90% of the baseline heart rate. Any other percentage may be used, however. In the example of FIG. 2, assuming a baseline average heart rate of 60 beats per minute, the threshold heart rate can be calculated as 54 beats per minute (90% of 60 beats per minute).

At portion 220, the driver's heart rate drops to about 52 beats per minute. Because this drop dips below the threshold heart rate of 54 beats per minute, the sleep prevention program is initiated. In some examples, the drop below the threshold heart rate indicates a pre-sleep event. In such cases, the driver can fall asleep in a matter of seconds. As a result, the sleep prevention program can be initiated immediately to wake the driver.

Portion 230 reflects initiation of the sleep prevention program. This can include any number of features, such as audio and visual warnings, as discussed above. In some examples, a tactile warning can be used as well, or in addition to, the audio and visual warnings. For example, the driver can experience a vibration caused by a personal device, heart-rate monitor, or car seat. As shown in FIG. 2, initiation of the sleep prevention program causes the driver's heart rate to immediately jump to over 80 beats per minute. The jump can be cause by the startling audio and/or visual warnings, as well as the realization that the driver almost fell asleep at the wheel.

At portion 240, the driver's heart rate remains elevated related to portion 210. The elevated heart rate is due, at least in part, to the sleep prevention program. In particular, the sleep prevention program can provide various activities to keep the driver alert and awake. As explained earlier, these activities include examples such as audio-based games, a virtual conversation, a phone call with a contact, and other activities designed to keep a driver alert and occupied without distracting the driver from actually driving.

Figure 3:
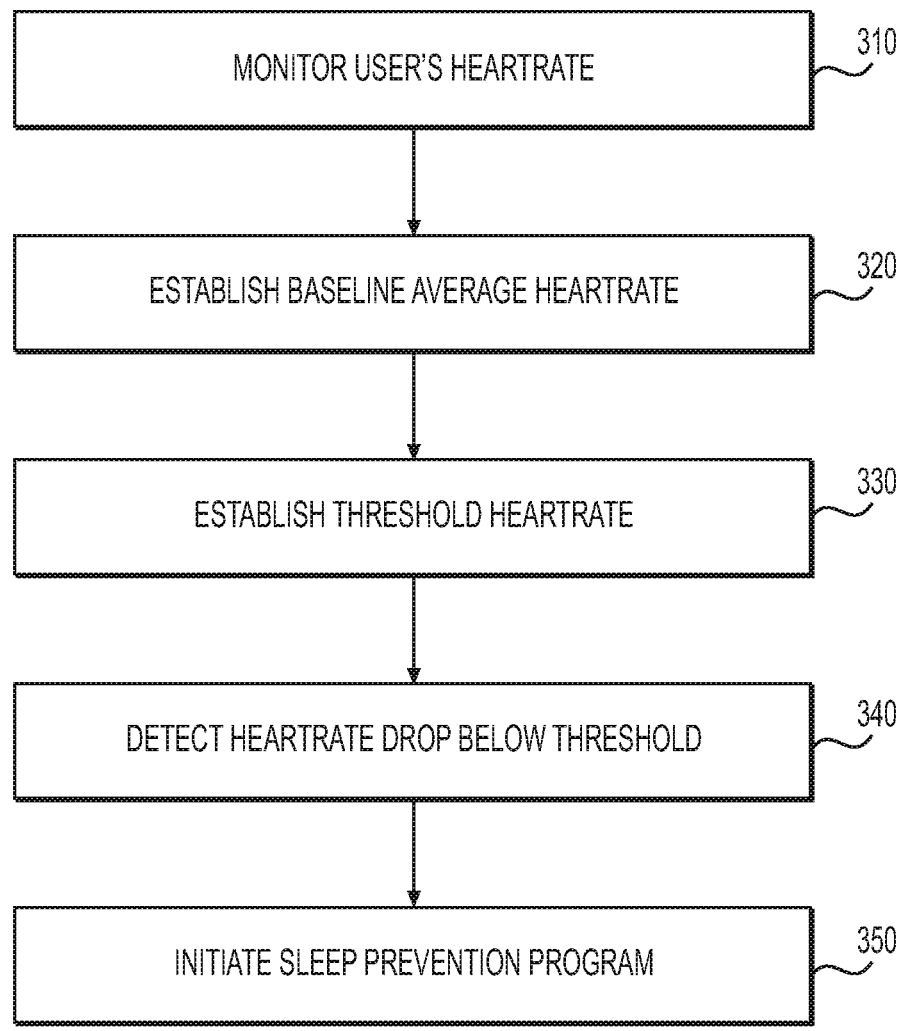
FIG. 3 is a flowchart of an exemplary method for detecting and preventing sleep onset in a user.

FIG. 3 depicts a flowchart of an example method for detecting and preventing sleep onset in a user. At stage 310, the system monitors the user's heart rate. This can be accomplished through any viable method, such as with a body-worn heart-rate monitor described in conjunction with FIG. 1. The heart-rate monitor can be paired with a computing device, such as a personal device or a vehicle's onboard computer, to assist in monitoring the user's heart rate.

Stage 320 includes establishing a baseline average heart rate for the user. The baseline average heart rate can be calculated by averaging the user's heart rate over a period of time, as described above with respect to FIG. 2. For example, the baseline average heart rate can be calculated by averaging the user's heart rate over a three-minute period of time. The baseline average heart rate can be recalculated after a defined period of time such that the system maintains up to date information on the user.

Stage 330 includes establishing a threshold heart rate based on the calculated baseline average heart rate. Any percentage that indicates sleep onset may be used. For example, the threshold heart rate can be chosen as 90% of the baseline average heart rate. Other percentages can be used, such as between 80-95%. The particular percentage can be optimized for different users based on feedback or other information from individual users. For example, a user can enroll in a calibration program that monitors a user's sleep patterns. In another example, a user can provide feedback on previous sleep prevention programs, indicating their level of drowsiness when the sleep prevention program initialized.

Stage 340 includes detecting a heart rate drop below the threshold heart rate. This can include, for example, comparing the user's current heart rate to the threshold heart rate. If the user's current heart rate is below the threshold, then the method can include carrying out stage 350.

Stage 350 includes initiating a sleep prevention program. Because a user may fall asleep almost immediately after their heart rate drops, the sleep prevention program can be initiated within a matter of seconds, if not less, of detecting a heart rate drop below the threshold level. The sleep prevention program can include a variety of different strategies for keeping a user awake, as described with respect to FIG. 1. For example, the sleep prevention program can include displaying an alert on a display in a vehicle, playing a sound through a vehicle speaker or personal device, initiating a verbal-based game with the user, initiating a telephone call, conducting a virtual conversation, and/or displaying a blue light, with wavelengths between about 450 nm and 495 nm. Of course, the sleep prevention program can include more than one of these features if desired.

Other examples of the disclosure will be apparent to those skilled in the art from consideration of the specification and practice of the examples disclosed herein. Though some of the described methods have been presented as a series of steps, it should be appreciated that one or more steps can occur simultaneously, in an overlapping fashion, or in a different order. The order of steps presented are only illustrative of the possibilities and those steps can be executed or performed in any suitable fashion. Moreover, the various features of the examples described here are not mutually exclusive. Rather any feature of any example described here can be incorporated into any other suitable example.

Furthermore, though the aforementioned systems and methods for detecting sleep onset and initiating sleep prevention programs are described in the context of a vehicle and a driver, the systems and methods described herein can be implemented in other contexts. For example, the systems and methods described here can be used by security guards or military personnel tasked with remaining vigilant through a night shift, anesthesiologists or other medical professionals that need to remain alert during a procedure, or in any other suitable context in which a person may become drowsy due to prolonged periods of inactivity.

It is intended that the specification and examples be considered as exemplary only, with a true scope and spirit of the disclosure being indicated by the following claims.

What is claimed is:

1. A method for detecting and preventing sleep onset in a user, comprising:
   monitoring a user's heart rate;
   establishing a baseline average heart rate for the user over a period of time;
   calculating a threshold heart rate based on the baseline average heart rate, wherein the threshold heart rate is less than the baseline average heart rate;
   determining that the user's heart rate is below the threshold; and
   alerting the user.

2. The method of claim 1, wherein alerting the user comprises initiating a sleep prevention program.

3. The method of claim 2, wherein initiating the sleep prevention program comprises playing a sound through at least one speaker in a vehicle.

4. The method of claim 2, wherein initiating the sleep prevention program comprises initiating a verbal-based game with the user.

5. The method of claim 2, wherein initiating the sleep prevention program comprises initiating a telephone call with a contact of the user.

6. The method of claim 2, wherein initiating the sleep prevention program comprises conducting a virtual conversation with the user.

7. The method of claim 2, wherein initiating the sleep prevention program comprises a displaying a light comprising wavelengths between about 450 nm and 495 nm.

8. The method of claim 1, wherein establishing the baseline average heart rate over a period of time comprises averaging the user's heart rate over a span of at least 3 minutes.

9. The method of claim 1, further comprising reestablishing the baseline average heart rate and recalculating the threshold heart rate, based on the reestablished baseline average heart rate, every 3 minutes.

10. The method of claim 1, wherein calculating the threshold heart rate comprises calculating a value that is 90% of the baseline average heart rate.

11. A system for detecting and preventing sleep onset in a user, comprising:
   a wearable heart rate monitor;
   a non-transitory, computer-readable medium that contains instructions;
   a processor, communicatively coupled to the heart rate monitor, that executes the instructions to perform stages including:
      monitoring a user's heart rate;
      establishing a baseline average heart rate over a period of time;
      calculating a threshold heart rate based on the baseline average heart rate, wherein the threshold heart rate is less than the baseline average heart rate;
      determining that the user's heart rate is below the threshold; and alerting the user.

12. The system of claim 11, wherein alerting the user comprises initiating a sleep prevention program.

13. The system of claim 11, wherein initiating the sleep prevention program comprises playing a sound through at least one speaker in a vehicle.

14. The system of claim 12, wherein initiating the sleep prevention program comprises initiating a verbal-based game with the user.

15. The system of claim 12, wherein initiating the sleep prevention program comprises initiating a telephone call with a contact of the user.

16. The system of claim 12, wherein initiating the sleep prevention program comprises conducting a virtual conversation with the user.

17. The system of claim 12, wherein initiating the sleep prevention program comprises a displaying a light comprising wavelengths between about 450 nm and 495 nm.

18. The system of claim 11, wherein establishing the baseline average heart rate over a period of time comprises averaging the user's heart rate over a span of at least 3 minutes.

19. The system of claim 11, wherein the stages further comprise reestablishing the baseline average heart rate and recalculating the threshold heart rate, based on the reestablished baseline average heart rate, every 3 minutes.

20. The system of claim 11, wherein calculating a threshold heart rate comprises calculating a value that is 90% of the baseline average heart rate.

* * * * *